United States Patent

Matravers et al.

[11] Patent Number: 6,099,591
[45] Date of Patent: Aug. 8, 2000

[54] METHOD AND COMPOSITION FOR HAIR COLORING USING GREEN TEA POLYPHENOLS

[75] Inventors: Peter Matravers, Plymouth; Ulrich Milius, Coonrapids; Tracy L. Cornuelle, Saint Paul, all of Minn.

[73] Assignee: Aveda Corporation, Blaine, Minn.

[21] Appl. No.: 09/015,461

[22] Filed: Jan. 29, 1998

[51] Int. Cl.[7] .................................................. A61K 7/13
[52] U.S. Cl. ......................... 8/408; 8/407; 8/410; 8/411; 8/412; 8/424; 8/576; 8/613
[58] Field of Search ................................ 8/406, 407, 408, 8/410, 411, 412, 424, 576, 613

[56] References Cited

U.S. PATENT DOCUMENTS

| | | | |
|---|---|---|---|
| 4,013,404 | 3/1977 | Parent et al. | 8/423 |
| 4,517,175 | 5/1985 | Iwabuchi et al. | 8/405 |
| 5,131,912 | 7/1992 | Ehara et al. | 8/421 |

FOREIGN PATENT DOCUMENTS

| | | |
|---|---|---|
| 124393 | 11/1994 | European Pat. Off. . |
| 9-263522 | 10/1997 | Japan . |

OTHER PUBLICATIONS

English language translation of JP–9–263,522, Lion Corp, pp. 1–18, Oct. 1997.
Venkataraman, The Chemistry of Synthetic Dyes, vol. 5, pp. 478–479, 1971 (no month available).

*Primary Examiner*—Caroline D. Liott
*Attorney, Agent, or Firm*—Richard R. Mybeck

[57] ABSTRACT

A hair coloring composition, and a method for using the composition in which a natural plant-derived chemical of the formula

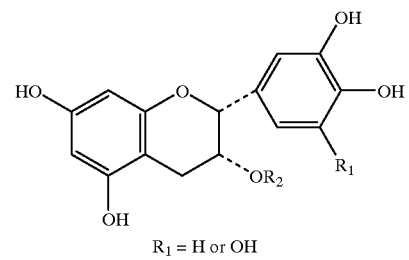

$R_1 = H$ or $OH$

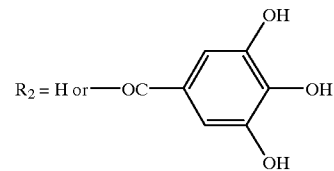

$R_2 = H$ or $-OC-$ is employed as a coupler-modifier in a composition containing a primary intermediate and a customary coupler. The novel coupler-modifiers produce a composition which is more physiologically suitable for use in hair colorings than the prior art compositions and allows for the preparation of compositions which produce highly stable colorings over a broad range shades and tones.

13 Claims, No Drawings

METHOD AND COMPOSITION FOR HAIR COLORING USING GREEN TEA POLYPHENOLS

INTRODUCTION

The present invention relates generally to compositions and methods for the oxidative coloring of hair using green tea polyphenols as coupler-modifiers. The green tea polyphenols used herein may include one or more of the following polyphenols: epigallocatechin gallate, epigallocatechin, epicatechin gallate, or epicatechin.

BACKGROUND OF THE INVENTION

Oxidative coloring methods and compositions have had tremendous significance for the coloring of human hair. Coloring takes place through the reaction of one or more primary intermediates with one or more couplers in the presence of a suitable oxidation agent. In particular, the oxidation agent is added to a mixture of one or more primary intermediates and one or more couplers shortly before application to the human hair. The oxidation agent then stimulates an oxidation condensation reaction between the one or more primary intermediates and the one or more couplers to form the colored dye molecules in situ on the hair.

For the purposes of this specification, the following lexicon shall apply. Oxidative dyes (sometimes called para-dyes) are the substances used as permanent hair dyes. These are, for the most part, colorless or faintly colored compounds which are transformed into a colored material in situ on the hair. When mixed with oxidizing agents these oxidative dyes produce colored compounds or colorants through a process of oxidative condensation. There are two types of oxidative dye intermediates which are used in combination to produce permanent hair colors, these are the primary intermediates and the couplers. In general, the oxidative dye intermediates are aromatic compounds belonging to several chemical families: diamines, aminophenols, aminonaphthols, phenols and naphthols.

Primary intermediates are aromatic compounds which are almost exclusively benzene derivatives, substituted by at least two electron-donor groups, such as amine or hydroxy groups, these being para or ortho to each other. This confers the property of easy oxidation. A primary intermediate combines with a coupler in an oxidative condensation reaction (sometimes called a coupling reaction) to form the colored dye molecules.

Couplers are also oxidative dye intermediates which are also aromatic compounds, and couplers are also almost exclusively benzene derivatives substituted by the same groups as the primary intermediates. However, couplers are substituted in meta position to each other. In this position it should be noted that the couplers do not have the property of easy oxidation. A coupler combines with a primary intermediate in a condensation reaction to produce the colored dye molecules.

Coupler-modifiers are, per the present invention, substances which are added to the oxidative condensation reaction in addition to the primary intermediates and the couplers as discussed above. It is not known how a coupler-modifier participates in the condensation reaction; but, it has been discovered that coupler-modifiers do affect the final hair color produced by a condensation reaction.

Oxidation agents are peroxide compounds which are added to a mixture of one or more primary intermediates with one or more couplers to stimulate the oxidation condensation reaction to occur quickly. The oxidation agent is added to the primary intermediate/coupler mixture shortly before applying the dye mixture to the hair.

In oxidative coloring, numerous primary intermediates have been employed. Examples include 1,4-diaminobenzene, 2,5-diaminotoluene, 3-methyl-4-aminophenol, N,N-bis-(2-hydroxyethyl)-p-phenylenediamine, and p-aminophenol. Similarly, numerous couplers, such as resorcinol, 4-chlororesorcinol, 1-naphthol, 2,4-diaminotoluene, 2,4-diaminophenoxyethanol, 2,5-dimethylphenol, methyl resorcinol, m-phenylenediamine, 2,6-diaminopyridine, and m-aminophenol, inter alia, have been used. Oxidation agents have included urea peroxide, melamine peroxide or hydrogen peroxide; however, hydrogen peroxide has been the preferred oxidation agent.

Chemical substances to be used for the coloring of human hair must meet numerous minimum requirements. For example, these substances must be toxicologically and dermatologically suitable for such use. Additionally, they must also provide the desired intensity of color and provide a broad palette of various color nuances. Further, good tolerances to light, and/or acid exposure, permanent wave treatments, and physical rubbing are required. In any event, the hair colorings should remain stable over a period of at least 4 to 6 weeks without negative influence from light, rubbing and/or chemical agents.

This large number of requirements has not been fully or satisfactorily met through the use of known oxidation hair coloring substances. This is particularly true for the phenolic couplers 1-naphthol, 2,5-dimethylphenol, m-phenylenediamine as well as derivatives 2,4-diaminotoluene and 2,4-diaminophenoxyethanol.

BRIEF SUMMARY OF THE INVENTION

As shown herein, certain green tea polyphenols have been found to perform beneficially when admixed into oxidative dye compounds. In particular, the natural, plant-derived green tea polyphenols of the formula

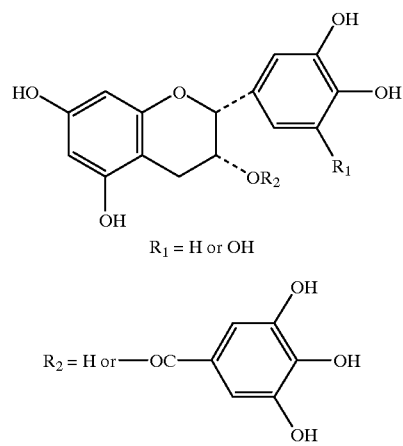

are used as coupler-modifiers in addition to the conventional couplers heretofore employed in the oxidative condensation reaction.

Accordingly, it is an object of the present invention to provide novel oxidative dye compositions for use in the coloring of hair.

It is also an object to provide oxidative dye components which possess good physiological properties and which, in combination with known primary intermediates such as 1,4-diaminobenzene, 2,5-diaminotoluene, N,N-bis-(2-hydroxyethyl)-p-phenylenediamine, p-aminophenol; and couplers such as resorcinol, 4-chlororesorcinol, 1-naphthol, 2,4-diamino-toluene, 2,4-diaminophenoxyethanol, 2,5-dimethylphenol, methyl resorcinol, m-phenylenediamine, 2,6-diaminopyridine, and m-aminophenol; a unique coupler-modifier such as epigallocatechin gallate, epigallocatechin, epicatechin gallate, or epicatechin is added to provide coloring with good wear properties and desired color intensity.

It is also an object of the present invention to provide a method for using the novel compositions for the coloring of human hair.

These and still further objects, as shall hereinafter appear, are readily fulfilled by the present invention in a remarkably unexpected manner as will be readily discerned from the following detailed description of an exemplary embodiment thereof.

DESCRIPTION OF THE PREFERRED EMBODIMENT

It has been found that these objects can be achieved by the addition of green tea polyphenols of the general formula

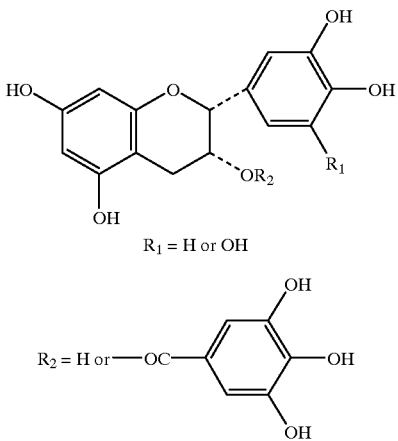

$R_1$ = H or OH $R_2$ = H or —OC— (3,4,5-trihydroxyphenyl)

as coupler-modifiers to oxidative dye compositions for use in oxidative condensation reaction coloring of human hair. The compounds used as coupler-modifiers in the present invention hair coloring compositions, are known as green tea polyphenols which are also known as epicatechin, epicatechin gallate, epigallocatechin and epigallocatechin gailate. These polyphenols are soluble in water. When used as coupler-modifiers, the green tea polyphenols of the above-presented general formula will be present in a concentration of between about 0.01 to 5.0 weight-percent, preferably between about 0.01 to about 3 weight-percent.

Examples of primary intermediates which can be used in the hair coloring compositions of the present invention are p-aminophenol, 3-methyl-4-amino-phenol, 1,4-diaminobenzene, 2,5-diaminotoluene, N,N-bis-(2-hydroxyethyl)-p-phenylenediamine and 2,5-diaminobenzyl alcohol.

The hair coloring compositions of the present application may also contain additional known couplers such as resorcinol, 4-chlororesorcinol, m-aminophenol, 3,4-diaminobenzoic acid, 2,6-diaminopyridine, and 6-methyl-3-aminophenol.

In producing the novel composition of the present invention, the coupler is combined with the primary intermediate into a coupler/primary intermediate mixture. The coupler component of the coupler/primary intermediate mixture is added in general in approximately an equimolar amount with reference to the primary intermediate. It is, nonetheless, not disadvantageous for the coupler component of the coupler/primary intermediate mixture to be present in excess. It is further not necessary that the coupler/primary intermediate mixture consist of only a single primary intermediate or a single coupler: in many cases, the mixture may include a number of primary intermediates and couplers. To this mixture, the coupler-modifier is added as will be hereinafter described in greater detail.

The total amount of oxidation coloring agents in the mixtures of the present invention should advantageously be between about 0.1 and 5.0 weight-percent, preferably 0.5 to 3.0 weight-percent of the total mixture.

In addition, it is possible to add known, directly-applicable coloring agents to the compositions, such as triphenylmethane such as DIAMOND FUCHSIN (C.I. 42 510) and LEATHER RUBY HF (C.I. 42 520), aromatic nitro dyes such as 2-nitro-1,4-diaminobenzene, azo dyes like dyes such as 2-nitro-1,4-diaminobenzene, azo dyes like ACID BROWN 4 (C.I. 14 805), anthraquinone dyes such as DISPERSE RED 15 (C.I. 60 710), BASIC BLUE 99 (C.I. 56059), BASIC BROWN 16 (C.I. 12250), BASIC RED 76 (C.I. 12245), BASIC YELLOW 57 (C.I. 12719), or 1,4,5,8-tetraaminoanthraquinone and 1,4-diaminoanthraquinone.

Further additional cosmetic additives, such as antioxidants like ascorbic acid, erythorbic acid, or sodium sulfite; and alkali hydroxides; complex-forming agents; perfume oils; wetting agents; emulsifiers; thickeners; and hair care agents may be present in the mixtures of the present invention when desired.

The application form may be a solution, but preferably will be a gel, a creme or an emulsion. The preparation involves mixing the coloring components with the customary components of the particular application form. Such customary components in cremes, emulsions or gels include wetting agents or emulsifiers from the class of anionic or nonionic surface active substances such as fatty alcohol sulfates, fatty acid alkanolamides, alkyl sulfonates, alkyl benzene sulfonates, oxethylated fatty alcohols, oxethylated nonyl phenols, as well as thickeners such as higher fatty alcohols, fats, cellulose derivatives, paraffin oil and fatty acids, or other hair care agents such as lanolin derivatives, cholesterin and pantothenic acid. These additives are used in amounts customary for such compositions; for example, the wetting agents and emulsifiers are present in concentrations between about 0.5 to 30 weight-percent, while thickeners may comprise between about 0.1 to 25 weight-percent of the composition.

Depending upon the particular components, the coloring compositions of the invention may react under slightly acidic, neutral or alkaline conditions. In particular, they often have a pH value in the alkaline range between 8.0 and 11.5, in which case the preparation usually takes place with ammonia. Nevertheless, other known organic amines, such as monoethanolamine or triethanolamine, can also be used.

In the current process for oxidative coloring of hair, the oxidative coloring composition is a mixed combination of a customary primary intermediate and a coupler with a green tea polyphenol of the above general formula as a coupler-modifier. Then, the primary intermediate/coupler/coupler-modifier mixture is mixed with an oxidation agent shortly prior to use, and the primary intermediate/coupler/coupler-modifier/oxidation agent mixture is then applied to the hair. The preferred oxidation agent for development of the hair color is hydrogen peroxide, for example, as a 6% aqueous solution. Alternatively, its addition products such as urea, melamine or sodium borate can be used. The mixture is allowed to work on the hair at between about 15° and 50° C. for about 10 to 45 minutes, after which the hair is rinsed with water and dried. If desired, after rinsing the hair may be washed with shampoo and rinsed with a weak organic acid, such as citric or tartaric acid.

The compositions thus obtained using a green tea polyphenol as a coupler-modifier lead to hair colorings with excellent fast to wear properties, including stability in exposure to washing, rubbing, and light. Further, the hair colorings can be removed through the use of reducing agents.

With respect to color possibilities, the novel compositions provide a broad palette of various colors, depending upon type and composition, which range from silver to green.

Particularly interesting is the fact that as coupler-modifiers, green tea polyphenols can be used as nuancers when one or more couplers are present in excess.

The invention may be better understood through the following examples:

EXAMPLE 1

| Hair coloring solution |
| --- |
| 1.0 g green tea polyphenols |
| 1.6 g p-aminophenol |
| 1.6 g resorcinol |
| 1.2 g sodium hydroxide, 50% |
| 0.4 g sodium sulfite, anhydrous |
| 10.0 g ammonium lauryl sulfate, (28% aqueous solution) |
| 10.0 g ethanol |
| 10.0 g ammonia, 26% |
| 64.2 g water |
| 100.0 g total |

Shortly before application 10 g of this hair coloring composition is mixed with 10 ml hydrogen peroxide solution (6%). The mixture is allowed to react for 30 minutes at 30° C. in blond human hair. Thereafter, the hair is rinsed with water and dried. The hair has a light olive coloration.

EXAMPLE 2

| Hair coloring solution |
| --- |
| 1.0 g green tea polyphenols |
| 1.6 g N,N-bis-(2-hydroxyethyl)-p-phenylenediamine |
| 0.6 g resorcinol |
| 1.2 g sodium hydroxide, 50% |
| 0.4 g sodium sulfite, anhydrous |
| 10.0 g ammonium lauryl sulfate (28% aqueous solution) |
| 10.0 g ethanol |
| 10.0 g ammonia, 26% |
| 65.2 g water |
| 100.0 g total |

Shortly before application 10 g of this hair coloring composition is mixed with 10 ml hydrogen peroxide solution (6%). The mixture is allowed to react for 30 minutes at 30° C. in blond human hair. Thereafter, the hair is rinsed with water and dried. The hair has a luminous silver coloration.

EXAMPLE 3

| Hair coloring composition in gel form |
| --- |
| 1.0 g green tea polyphenols |
| 0.4 g p-phenylenediamine |
| 0.4 g m-aminophenol |
| 0.4 g sodium hydroxide, 50% |
| 0.4 g sodium sulfite, anhydrous |
| 15.0 g oleic acid |
| 7.0 g ethanol |
| 10.0 g ammonia, 26% |
| 65.4 g water, completely salt-free |
| 100.0 g total |

Ten (10) g of the above hair coloring mixture is mixed shortly before application with 10 ml 6% hydrogen peroxide solution; the mixture is then applied to blond human hair. After a period of 30 minutes at 30° C. the hair is rinsed with water and dried. The hair is colored in an olive brown tone.

EXAMPLE 4

| Hair coloring composition in creme form |
| --- |
| 1.00 g green tea polyphenols |
| 0.50 g 2,5-diaminotoluene, with 1 Mol H2SO4 per Mol diamine |
| 0.45 g resorcinol |
| 0.26 g sodium hydroxide, 50% |
| 0.30 g sodium sulfite, anhydrous |
| 3.50 g ammonium lauryl sulfate (28% aqueous solution) |
| 15.00 g cetyl alcohol |
| 10.00 g ammonia, 26% |
| 68.99 g water |
| 100.0 g |

Shortly before use 10 g of this hair coloring composition is mixed with 10 ml hydrogen peroxide solution (6%) and allowed to remain in blond human hair for 30 minutes at 30° C. The hair is then rinsed with water and dried. The hair has an ash blond coloring.

All of the above percentages are in terms of weight percent.

From the foregoing, it is readily apparent that a new and useful hair coloring composition and method of using same has been herein described and illustrated which fulfills all of the aforestated objects in a remarkably unexpected fashion. It is of course understood that such modifications, alterations and adaptations as may readily occur to the artisan confronted with this disclosure are intended within the spirit of this disclosure which is limited only by the scope of the claims appended hereto.

Accordingly, what is claimed is:

1. A composition for oxidative coloring of hair comprising a mixture containing a primary intermediate characterized by the ability to produce color on the hair in the presence of hydrogen peroxide and selected from the group consisting of: 2,5-diaminotoluene, 3-methyl-4-amino-phenol, 2,5-diaminobenzyl alcohol, 1,4-diaminobenzene, p-aminophenol, and N,N-Bis-(2-hydroxyethyl)-p-phenylenediamine; a coupler selected from the group consisting of resorcinol, 4-chlororesorcinol, m-aminophenol, 3,4-diaminobenzoic acid, 1-naphthol, m-aminophenol, and 5-amino-2-methylphenol, and a coupler-modifier selected from the group consisting of epigallocatechin gallate, epigallocatechin, epicatechin gallate and epicatechin.

2. A composition according to claim 1 in which said coupler-modifier is present in a concentration between 0.01 and 5.0 weight-percent.

3. A composition according to claim 1 in which said coupler-modifier is present in a concentration between 0.1 and 3.0 weight-percent.

4. A composition according to claim 1 in which the primary intermediate/coupler mixture comprises 0.1 to 5.0 weight-percent of the composition.

5. A composition according to claim 1 in which the primary intermediate/coupler mixture comprises 0.5 to 3.0 weight-percent of the composition.

6. A composition according to claim 1 containing at least one directly-applicable coloring agent selected from the group consisting of: 2-nitro 1,4-diaminobenzene, DISPERSE RED 15 (C.I. 60710), BASIC BLUE 99 (C.I. 56059), BASIC BROWN 16 (C.I. 12250), BASIC RED 76 (C.I. 12245), BASIC YELLOW 57 (C.I. 12719), 1,4,5,8-tetraaminoanthraquinone and 1,4-diamino-anthraquinone.

7. A composition according to claim 1 containing at least one antioxidant.

8. A composition according to claim 7 in which said antioxidant is selected from the group consisting of ascorbic acid, erythorbic acid, and sodium sulfite.

9. A composition according to claim 1 further comprising wetting agents or emulsifiers selected from the class of anionic and nonionic surface active substances or thickeners selected from the group consisting of higher fatty alcohols, fats, cellulose derivatives, paraffin oil and fatty acids.

10. A process for oxidative coloring of hair comprising forming an oxidizable mixture of a primary intermediate which is capable of producing color on the hair in the presence of hydrogen peroxide and comprising at least one reagent selected from the group consisting of 2,5-diaminotoluluene, 1,4-diaminobenzene, p-aminophenol, 3-methyl-4 amino-phenol, 2,5-diaminobenzyl alcohol and N,N-Bis-(2-hydroxyethyl)-p-phenylenediamine, a coupler selected from the group consisting of resorcinol, 4-chlororesorcinol, m-aminophenol, 3,4-diaminobenzoic acid, 1-naphthol, m-aminophenol, and 5-amino-2-methylphenol, and a coupler-modifier of the formula:

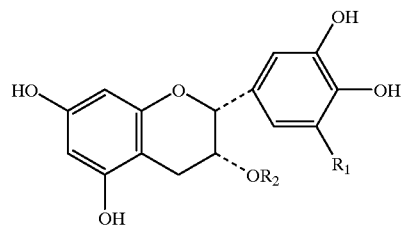

wherein: $R_1$ = H or OH $R_2$ = H or 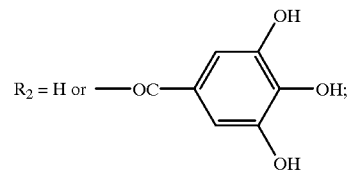

combining said oxidizable mixture with an oxidation agent to form a combination;

applying said combination to hair;

letting said combination react on said hair for a period of from about 10 to about 45 minutes at a temperature between 15° to 50° C.;

rinsing said hair, and drying the hair.

11. A process according to claim 10 wherein said oxidation agent is hydrogen peroxide.

12. A process according to claim 10 in which said coupler-modifier is selected from the group consisting of epigallocatechin gallate, epigallocatechin, epicatechin gallate and epicatechin.

13. A process according to claim 10 in which said oxidizable mixture comprises at least two of said couplers.

* * * * *